(12) United States Patent
Pettit et al.

(10) Patent No.: US 8,024,986 B2
(45) Date of Patent: Sep. 27, 2011

(54) ENVIRONMENTAL SENSING UNIT

(75) Inventors: Casey Pettit, Portland, OR (US);
Mathew Vernon, Portland, OR (US);
Rich Soennichsen, Portland, OR (US)

(73) Assignee: Veris Industries, LLC, Portland, OR (US)

( * ) Notice: Subject to any disclaimer, the term of this patent is extended or adjusted under 35 U.S.C. 154(b) by 306 days.

(21) Appl. No.: 12/218,680

(22) Filed: Jul. 16, 2008

(65) Prior Publication Data

US 2009/0064759 A1 Mar. 12, 2009

Related U.S. Application Data

(60) Provisional application No. 60/993,220, filed on Sep. 10, 2007.

(51) Int. Cl.
*G01D 21/02* (2006.01)

(52) U.S. Cl. ............... 73/866.5; 73/23.2; 73/863.81

(58) Field of Classification Search ............... 73/866.5, 73/863.53, 863.81, 208, 209
See application file for complete search history.

(56) References Cited

U.S. PATENT DOCUMENTS

| | | | | |
|---|---|---|---|---|
| 3,354,716 A | * | 11/1967 | Wiebe et al. | 374/142 |
| 3,581,565 A | * | 6/1971 | Dieterich | 73/861.66 |
| 4,368,639 A | * | 1/1983 | Owens | 73/301 |
| 4,498,347 A | * | 2/1985 | Grantham et al. | 73/861.66 |
| 5,844,138 A | | 12/1998 | Cota | |
| 6,122,972 A | | 9/2000 | Crider | |
| 6,170,345 B1 | * | 1/2001 | Kerner | 73/866.5 |
| 6,241,950 B1 | * | 6/2001 | Veelenturf et al. | 422/103 |
| 6,516,676 B1 | * | 2/2003 | Mullowney, Jr. | 73/863.82 |
| 6,852,216 B2 | * | 2/2005 | Moscaritolo et al. | 210/85 |
| 6,941,193 B2 | * | 9/2005 | Frecska et al. | 700/276 |
| 7,421,911 B2 | * | 9/2008 | Desrochers et al. | 73/863.03 |
| 7,661,327 B2 | * | 2/2010 | Bourgein et al. | 73/865.9 |
| 2004/0182132 A1 | * | 9/2004 | Head | 73/23.2 |
| 2005/0066711 A1 | * | 3/2005 | Discenzo | 73/64.56 |
| 2006/0107774 A1 | * | 5/2006 | Meyberg | 73/866.5 |
| 2007/0137318 A1 | * | 6/2007 | Desrochers et al. | 73/863.81 |
| 2008/0178694 A1 | * | 7/2008 | Barford et al. | 73/866.5 |

OTHER PUBLICATIONS

Veris Industries Product Information Sheet, "H Series Probe Type Humidity Sensors 1% and 2% NIST, or Standard 2%, 3%, or 5%," 2006 Veris Industries, 2 pages.
Veris Industries Product Information Sheet, "HW Series Wall Mount Humidity Sensors 1%, 2%, 3%, or 5% Accuracy—Nist certificates available for 1% & 2% Models," 2006 Veris Industries, 2 pages.
Veris Industries Product Information Sheet, "PX Series Digital Pressure Transducer Dry Media," 2007 Veris Industries, 1 page.
Veris Industries Product Information Sheet, "PW2 Series 2-Wire 4-20mA Differential Pressure Transducer—Wet Media," 2006 Veris Industries, 2 pages.
Veris Industries, "Installation Instructions for PW2 Series 2-Wire, 4-20mA Differential Pressure Transducer Wet Media," 2006 Veris Industries, 2 pages.

* cited by examiner

*Primary Examiner* — Lisa Caputo
*Assistant Examiner* — Punam Roy
(74) *Attorney, Agent, or Firm* — Chernoff, Vilhauer, McClung & Stenzel

(57) ABSTRACT

A duct mounted environmental sensing unit includes a plurality of sensors for detecting respective parameters of a fluid in a duct. The sensing unit enables at least three sensors to make contact with the fluid through a single insertion point in the duct.

14 Claims, 4 Drawing Sheets

ENVIRONMENTAL SENSING UNIT

CROSS-REFERENCE TO RELATED APPLICATIONS

This application claims the benefit of U.S. Provisional App. No. 60/993,220, filed Sep. 10, 2007.

BACKGROUND OF THE INVENTION

The present invention relates to environmental sensors for detecting characteristics of a fluid in a duct and, more particularly, to a duct mounted environmental sensing unit for detecting a plurality of parameters of a fluid in a duct of a heating, cooling and ventilation system.

Temperature and humidity are primary factors in the comfort and quality of an indoor environment. While temperature is important to comfort, the humidity is a substantial factor in determining whether a specific temperature is comfortable. Temperature is commonly regulated as a function of the relative humidity in a space and humidifiers, to control the relative humidity, are often a part of the heating, cooling and ventilation systems of office buildings and industrial plants.

Carbon dioxide ($CO_2$) is a product of human respiration and, while high levels of carbon dioxide are toxic to humans, the concentration of carbon dioxide in an indoor environment is commonly used as a surrogate to indicate the presence of other indoor pollutants that may cause occupants to grow drowsy, have headaches, or function at a lower activity level. Since human respiration is a primary source of carbon dioxide in indoor environments, building codes typically specify the amount of outdoor air to be added to an interior space by the ventilation system on the basis of the occupancy of the space. In the past, ventilation systems commonly maintained a ventilation rate, at all times, that was sufficient for full occupancy of the space. However, heating, cooling, humidifying and moving this volume of air at times when the occupancy is low is wasteful of energy and expensive. Demand controlled ventilation seeks to vary the amount of outside air added to a space to optimize the comfort and well being of occupants and reduce energy consumption under conditions of variable and intermittent occupancy. Carbon dioxide concentration is used as an indicator of the occupancy and as a control parameter for demand controlled ventilation.

Relative humidity may be sensed by a sensor that comprises a polymer that is typically mounted on a porous ceramic plate and has a resistivity that changes as a function of the humidity. The accuracy of this type sensor is often insufficient for a ventilation system and the devices are subject to deterioration in harsh environments. A second type of humidity sensor employs a capacitor in which the dielectric comprises environmental air. Since the dielectric constant of air is one and the dielectric constant of water is approximately 80, changes in the relative humidity changes the dielectric constant of the air separating the capacitor plates, and, hence, the capacitance of the sensor. Variation in capacitance can be used in a number of ways in circuits to provide an electrical output that is indicative of the relative humidity. The accuracy of a system employing this type of sensor relies on the accuracy of the sensor's nominal capacitance which can be altered by the way in which the capacitor is shipped, handled or otherwise introduced to the environment.

Cota, U.S. Pat. No. 5,844,138, discloses a humidity sensing device that includes a humidity sensitive capacitor comprising part of an oscillator circuit. The frequency of the oscillator is a function of the capacitance of the humidity sensitive capacitor which, in turn, is a function of the relative humidity. The true capacitance of the humidity sensitive capacitor is measured against a known standard and stored in a memory in the humidity sensing device. A microprocessor uses the true capacitance data stored in the memory to correct the relative humidity measurements made with the device to account changes in capacitance resulting from aging or from shipping and handling of the device. A voltage divider network in the humidity sensing device provides temperature compensation for the relative humidity measurements. Cota also discloses an apparatus for supporting the humidity sensor in a stream of fluid flowing in a duct. An enclosure with an attached sleeve is bolted to the exterior of the duct with the sleeve projecting through a hole in the duct's wall. The humidity sensitive capacitor is secured in the end of a tube which passes through the sleeve. A swage nut compresses the sleeve to secure the tube and the humidity sensitive element in the fluid flowing in the duct.

Temperature is commonly measured with a thermistor or a resistance temperature detector (RTD) which exploit the predictable change in electrical resistance of certain materials when they are exposed to changing temperatures. Thermistors and RTDs can be very compact enabling a temperature sensor to be included with the humidity sensor in a mounting similar to that disclosed by Cota.

The presence of carbon dioxide is typically detected with either a chemical sensor or a non-dispersive infrared sensor. Chemical sensors comprise materials that are sensitive to the presence of $CO_2$ and while they typically consume little energy and can be miniaturized, they have a relatively short lifespan and are subject to drift effecting short and long term accuracy of the sensor. Non-dispersive infrared sensors comprise a source and a detector of infrared light disposed at opposite ends of a light tube and an interference filter to prevent light, with exception of light absorbed by the gas molecules of interest, from reaching the detector. A gas to be tested is introduced to the light tube and the absorption of a characteristic wavelength of light is measured to determine the presence of $CO_2$ in the gas. Non-dispersive infrared sensors can be expensive but are commonly used because no other known method works as reliably to detect $CO_2$. A $CO_2$ sensor can be mounted on a wall in the space to be monitored in a manner similar to the installation of a thermostat. The location of the sensor should be selected to expose the sensor to air that is indicative of general conditions within the occupied zone. Locations near doors, windows and air vents or close to where people would regularly sit or stand should be avoided because the $CO_2$ may be locally diluted by air from outside or concentrated by the local activity. A large number of wall mounted sensors are typically required because each sensor is only exposed to the local environment and at least one sensor is typically required in each space. Sensors for humidity and temperature may be combined with the wall mounted $CO_2$ sensor to reduce the number of sensor installations.

$CO_2$ sensors may also be installed on the ductwork of an air handling system to detect the concentration of $CO_2$ in the air flowing in the ducts, $CO_2$ sensors are typically located in the duct in which air is returning from a space but may also be mounted in the air intake for the ventilation system to measure the $CO_2$ in the intake air. While a ventilation system comprising a plurality of zones typically incorporates a number of sensors, a duct mounted sensor can serve a plurality of zones reducing the required number of sensors. Duct mounting of the $CO_2$ sensor is best applied where the ventilation system operates continuously and where the return airstream being monitored serves one or more zones that have similar levels of activity and occupancy at similar times. Combining a plurality of sensors in a single enclosure can be reduce the cost of the sensing units. Moreover, if a plurality of sensors can be installed at a single insertion point in a duct the number of entry points in the duct can be reduced reducing the chance of leakage and the cost of installation and maintenance.

What is desired, therefore, is an environmental sensing unit to enable a plurality of sensors to be installed at single insertion point in a duct of a ventilation system.

DETAILED DESCRIPTION OF PREFERRED EMBODIMENTS

Building codes commonly specify ventilation requirements for indoor spaces on a per-person basis. In the past, sufficient ventilation was provided at all times to satisfy the per person requirements of a fully occupied space. However, building occupancy varies throughout a day and often varies from day-to-day and considerable energy is required to heat, cool, humidify and move the replacement air. Providing full occupancy ventilation, even on a periodically varying basis, can be very energy inefficient and expensive. Demand controlled ventilation seeks to optimize occupant comfort and well being and energy consumption under conditions of variable and intermittent occupancy by varying the amount of outside air added to the space in response to changes in the occupancy. The level of carbon dioxide ($CO_2$) in the environment is an indicator of the presence of other pollutants that effect human performance and, since carbon dioxide is a product of human respiration, its concentration in the indoor environment is used by $CO_2$ demand controlled ventilation systems as an indicator of the occupancy in establishing ventilation rates necessary to satisfy the per person ventilation requirements for a space with variable occupancy.

In addition to supplying outside air to interior spaces, the air handling system typically heats, cools and modifies the humidity of the air circulating in a structure. Since comfort is a function of humidity as well as temperature, air handling systems commonly include sensors for both temperature and humidity.

In some applications, the $CO_2$ concentration, the humidity and the temperature are sensed with one or more sensing units mounted on the wall of the individual space(s) to be monitored. However, wall mounted sensing units are only exposed to the local conditions so at least one sensor for each parameter must be installed in each space to be monitored. The sensors are not inexpensive. In some applications, particularly where several spaces have the same or similar occupancy, or where the space is periodically remodeled and walls are moved, the cost of the ventilation system can be reduced by locating a sensing unit in the duct that carries the return air from the space(s). The present inventors realized that combining sensors for each of a plurality of environmental parameters, such as temperature, humidity and carbon dioxide concentration, in a single environmental sensing unit that could be installed at a single insertion point in a duct would substantially reduce the cost of installing and maintaining sensors for an air handling system.

Figure 1:
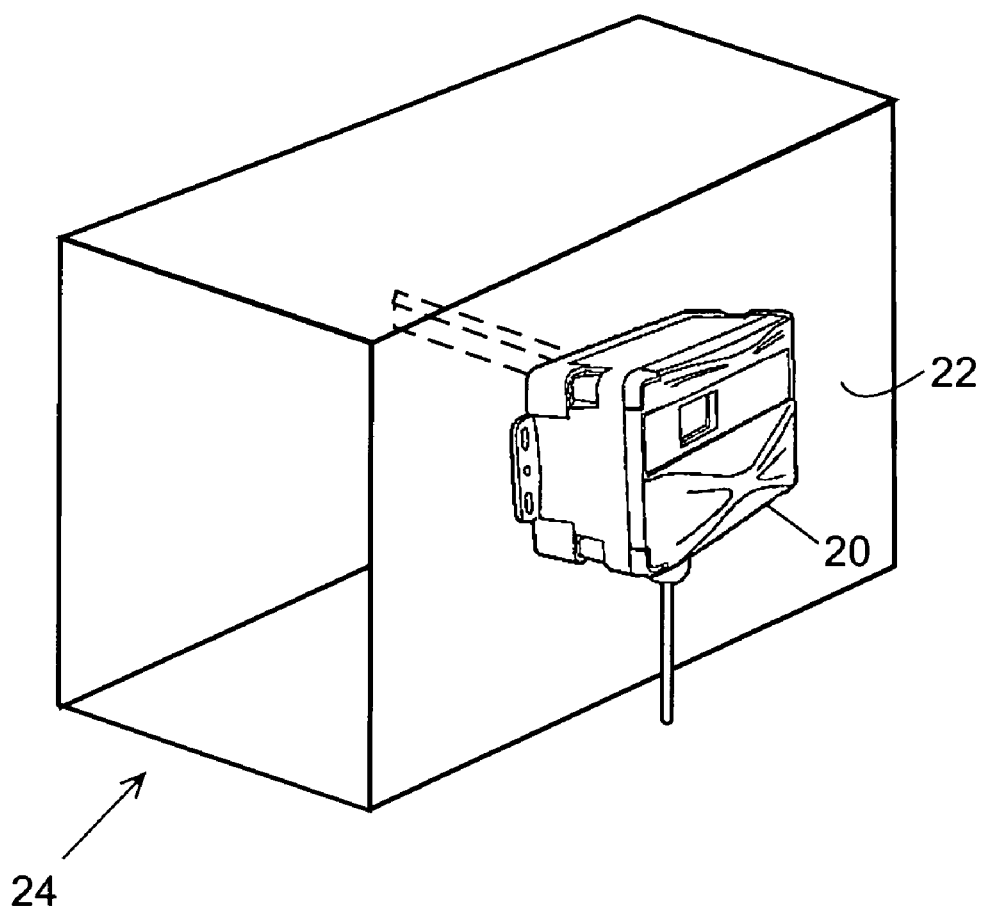
FIG. 1 is a perspective view of a portion of a duct and a duct mounted sensing unit.

Referring in detail to the drawings where similar parts are identified by like reference numerals, and, more particularly to FIG. 1, the environmental sensing unit 20 is mountable on the exterior surface of a wall 22 of a duct 24 to enable sensing of at least three characteristics of the fluid in the duct, for examples temperature, humidity, $CO_2$ concentration, carbon monoxide (CO) concentration, volatile organic compounds (VOC) and smoke. The construction of the sensing unit enables the installation of multiple sensors at a single insertion point in the duct reducing the cost of the sensor installation and eliminating potential leakage points.

Figure 2:
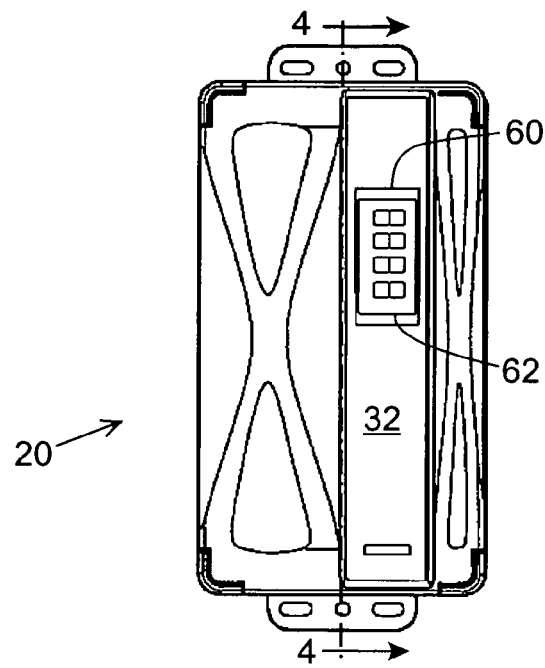
FIG. 2 is a top view of an environmental sensing unit.
Figure 3:
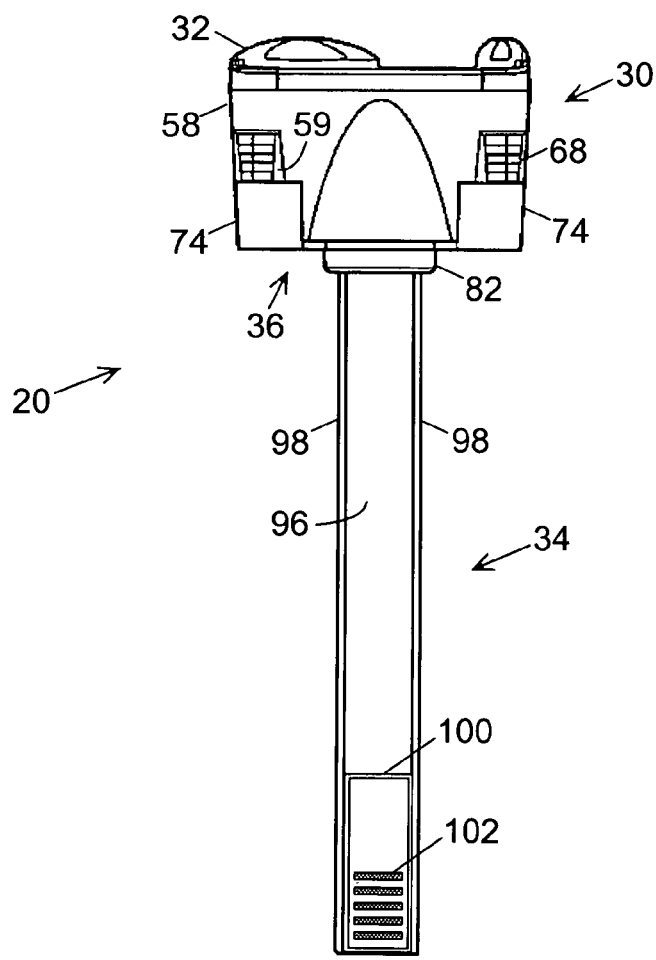
FIG. 3 is an elevation view of the environmental sensing unit of FIG. 2.

Referring also to FIGS. 2 and 3, the enclosure for the sensing unit comprises, generally, a housing 30, a cover 32, a rotatable sensor beam 34 and a mounting plate 36. While a number of materials would be suitable for use in construction of the enclosure, the major parts of the enclosure preferably comprise an insulating plastic, such as acrylonitrile butadiene styrene (ABS).

Figure 4:
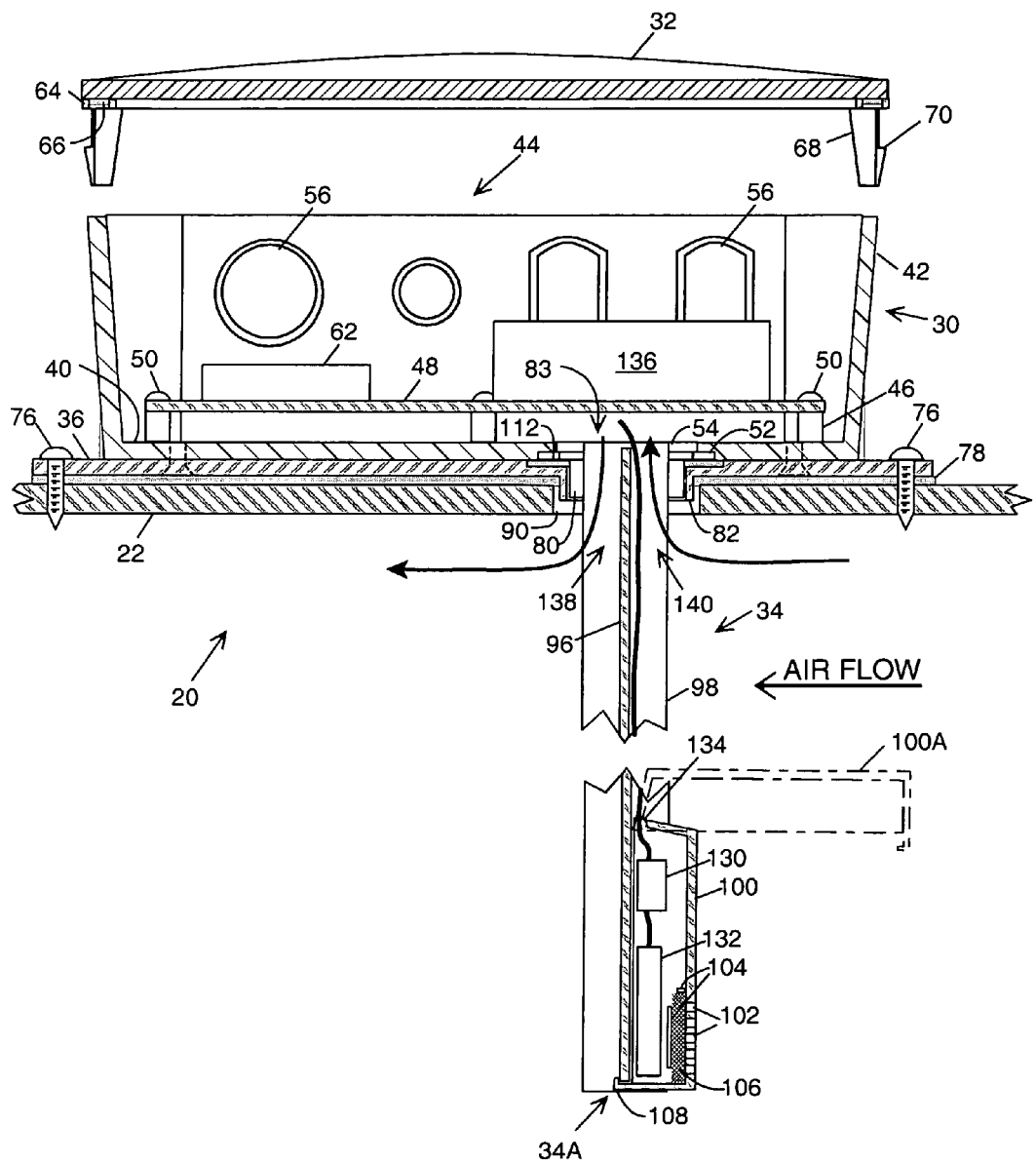
FIG. 4 is a section view of the environmental sensing unit along line 4-4 in FIG. 2.

Referring also to FIG. 4, the housing 30 comprises, generally, an open box having a generally rectangular base 40 with chamfered corners and a projecting wall 42 that encircles the perimeter of the base and defines an opening 44 that extends from the base to the exposed edge of the wall that is distal of the base. A plurality of standoffs 46 are molded on the interior surface of the base to support a circuit board 48 and enable the circuit board to be secured to the base with screws 50. The base defines a stepped aperture having a first, larger diameter aperture 52 that extends from the outside of the housing partially through the thickness of the base and a second smaller aperture 54 that extends coaxial with the first aperture through the remaining portion of the thickness of the base. The wall of the housing includes a plurality of portions defined by locally thin, inscribed wall sections or knockouts 56 enabling a user to create one or more apertures of predefined size and shape for connecting conduit or other electrical connectors to the housing by striking an inscribed portion of the wall to separate the knockout from the wall. In addition, a wall portion 58 proximate the exposed edge extends beyond the chamfered corner 59 of the wall to form a pocket between the extended portion of the wall and the chamfered wall portion.

The cover 32 is generally rectangular in shape and includes a window 60 through which a user can observe a display 62 mounted on a circuit board that is secured in the housing. The cover includes a groove portion 64 on the surface that will engage the exposed edge of the wall when the cover is installed on the base. The groove retains an elastomer seal 66 that is arranged to contact the exposed edge of the wall when the cover is in place on the housing to seal to the joint between the wall and the cover. A tapered stake portion 68 projects from the cover at each corner. The stake portions are arranged to slide into the pockets at the corners of the housing and include a surface 70 that will engage a corresponding surface of the pocket when the cover is in place securing the cover to the housing.

The mounting plate 36 is securable to the outside surface of the base of the housing by screws which engage the base. The mounting plate is generally rectangular and includes a mounting ear portion 72 that projects from each end of the mounting plate to permit the mounting plate and the attached housing to be secured to the wall 22 of a duct with screws 76. A gasket 78 interposed between the duct wall and the mounting plate seals the interface to prevent leakage. The mounting plate includes a projection 74 at each corner that is arranged to engage the outside of the wall of housing at the corner chamfers 59 to aid in aligning the mounting plate with the housing. The mounting plate also includes a portion defining an aperture 80 that is coaxially located with the aperture in the base of the housing. The aperture extends through a rim 82 that projects from the surface of the mounting plate that is proximate the duct wall forming an elongated cylindrical aperture. The coaxial apertures of the housing and the mounting plate form an enclosure aperture 83 providing a passage for fluid communication between the duct and the enclosed interior volume of the housing.

Figure 5:
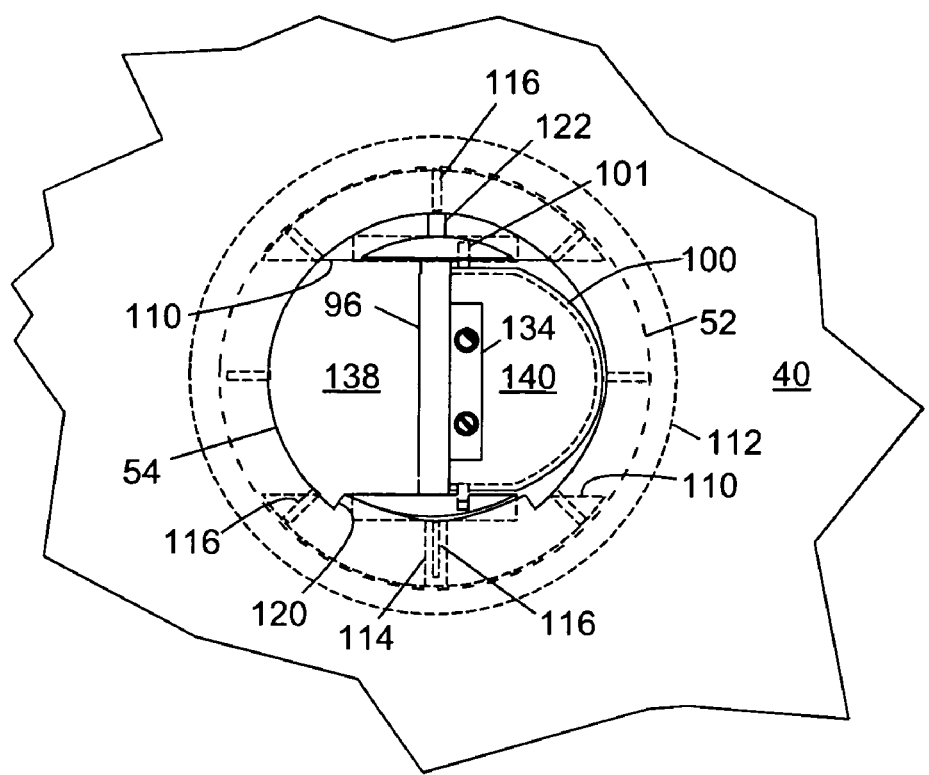
FIG. 5 is a top view of a portion of the base of the sensing unit housing and the sensor beam.

A rotatable sensor beam 34 is secured to the housing and projects from the surface of the mounting plate that interfaces with the wall of the duct. When the enclosure is installed on the wall of a duct, an aperture 90 is formed in the wall and the sensor beam is inserted through the aperture. The sensors for certain fluid parameters, for example humidity and temperature, are affixed proximate the projecting end 34A of the sensor beam so that when the enclosure is installed on the duct the sensors are supported in the fluid stream away from the boundary layer adjacent to the interior of the duct's wall. Referring also FIG. 5, the cross-section of the sensor beam is generally that of an I-beam comprising an elongate central web 96 with an elongate flange 98 affixed transverse to the web on each edge of the web.

A sensor housing 100 is attached to the end 34A of the sensor beam, distal of the housing, to enclose one or more sensors secured to the sensor beam. The sensor housing comprises, substantially, a wall forming an elongate, hollow cylinder half with enclosed ends. The sensor housing includes a plurality of grill slots 102 enabling fluid in the duct to be communicated with the enclosed sensors while preventing large particles in the fluid stream from entering the sensor housing. A plurality of projecting surfaces 104 on the inner surface of the sensor housing provides securement for a screen 106 that protects the interior of the sensor housing from particles that are small enough to pass through the grill slots. To facilitate cleaning of the screen and maintenance of the enclosed sensors, the sensor housing is hingedly attached to the sensor beam flanges by projecting hinge pins 101 that engage apertures in the flanges of the sensor beam. The end of the sensor housing distal of the hinge pins is secured to the web of the sensor beam by an flexible latch beam 108 that can be elastically deformed to disengage from the sensor beam permitting the housing to be opened allowing access to the sensors and the screen for cleaning or otherwise. The hinged connection retains the sensor housing to the sensor beam even when the housing is open 100A to avoid misplacing the sensor housing.

The sensor beam is rotatably secured to the housing of the sensing unit enabling the rotation of the sensor beam so that the web of the beam and the sensor housing can be aligned substantially normal to the flow of fluid in the duct without regard to the orientation of the housing on the exterior wall of the duct. The sensor beam passes through the aperture in the mounting plate until enlarged flange sectors 110, arranged transverse to the longitudinal axis of the sensor beam and projecting outward from the flanges of the beam, engage an elastic washer 112 on the surface of the mounting plate. When the mounting plate is engaged with the base of the housing and secured with screws, the flange sectors on the sensor beam are trapped between the base of the housing and the elastic washer interposed between the flange sectors and the mounting plate. The washer seals the interface between the base of the housing and the mounting plate and provides axial resiliency in the sensor beam mounting. A ridge 114 projecting from the upper surface of a flange sector engages the ones of a plurality of grooves 116 on the stepped surface of the aperture in the base of the housing. Engagement of the ridge and a groove under the resilient urging of the elastic washer provides a detent to maintain the rotational position of the sensor beam. A limiting sector 120, projecting radially into the aperture 54 in the base of the housing engages a stop lug 122 on the sensor beam to limit rotation of the sensor beam to less than one revolution to avoid twisting the wires that connect the sensor elements in the sensor housing with the circuit board in the sensing unit housing 30. The cylindrical inner surface of the rim 82 is arranged to engage a bearing surface sector formed on each of the outer surfaces of the sensor beam flanges to aid in supporting the sensor beam against lateral force created by the flowing fluid impinging on the web of the sensor beam.

One or more sensors 130, 132, such as a humidity sensitive capacitor, as disclosed by Cota, U.S. Pat. No. 5,844,138, and a temperature sensor, such as a thermistor or an RTD element, can be secured to the sensor beam in the sensor housing and connected to the circuit board in the sensing unit housing 30 by wires that pass through a wiring clearance slot 134 in the end of the sensor housing and extend along the web of the sensor beam. Other sensors 136, such as a non-dispersive, infrared carbon dioxide sensor can be attached to the circuit board or otherwise secured in the internal volume of the sensing unit housing 30. The I-beam cross-section of the sensor beam in conjunction with the substantially round apertures in the housing and the mounting plate forms two passages 138, 140 through which fluid in the duct is communicated with the interior of the sensing unit housing and any sensors mounted therein. When the sensor beam is rotated so that the web is transverse to the flow of fluid, a high pressure area is created on the upstream side of the flange and a low pressure area is created on the downstream side and the pressure differential between the two fluid passages 138, 140 causes fluid in the duct to flow into and out of the housing and into contact with the sensors enclosed in the housing.

The sensing unit with the pre-installed sensors is installed on the exterior wall of a duct by making a hole in the wall of the duct of sufficient size to accept the sensor beam probe and the rim on the mounting plate. The sensor beam is rotated so that the web of the beam is transverse to the flow of fluid in the duct and inserted into the hole in the duct wall. The mounting plate with the gasket interposed between the mounting plate and the duct wall is secured to the exterior of the duct wall by screws. An electrical connection is made to the circuit board in the enclosure and installation is complete.

The sensing unit enables at least three environmental sensors, to sense parameters of a fluid in a duct, to be installed through a single aperture in the duct wall substantially reducing the installation time and leakage possibilities for a ventilation system.

The detailed description, above, sets forth numerous specific details to provide a thorough understanding of the present invention. However, those skilled in the art will appreciate that the present invention may be practiced without these specific details. In other instances, well known methods, procedures, components, and circuitry have not been described in detail to avoid obscuring the present invention.

All the references cited herein are incorporated by reference.

The terms and expressions that have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims that follow.

We claim:

1. An environmental sensing unit responsive to a plurality of parameters of a fluid in an interior of a duct defined by a closed interior surface of a duct wall having an exterior surface, said duct wall including a portion defining a single duct wall aperture extending substantially normal to said exterior surface and connecting said exterior surface to said interior surface, said sensing unit comprising:
   (a) an enclosure defining an enclosable enclosure volume and including a portion defining one enclosure aperture, said enclosure arranged for attachment to said exterior of said duct wall with said enclosure volume in fluid communication with said interior of said duct through said duct wall aperture and said one enclosure aperture; and
   (b) at least three sensors in contact with said fluid through said single duct wall aperture, at least one of said at least three sensors located within said enclosure volume and not in contact with said fluid in said interior of said duct and at least one of said sensors supported in said fluid in said interior of said duct.

2. The environmental sensing unit of claim 1 wherein at least two of said sensors are supported on a sensor beam secured to said enclosure and arranged to protrude through said duct wall aperture into said fluid in said interior of said duct.

3. The environmental sensing unit of claim 2 wherein said sensor beam is supported for rotation by said enclosure.

4. The environmental sensing unit of claim 3 wherein said sensor beam further comprises a stop portion engageable with a portion of said enclosure to limit a range of rotation of said sensor beam to less than one revolution.

5. The sensing unit of claim 2 wherein said sensor beam further comprises a web arranged to divide said one enclosure aperture.

6. A sensing unit to detect a plurality of parameters of a fluid in an interior of a duct defined by a duct wall having a closed interior surface and an exterior surface, said duct wall including a portion defining a duct aperture extending substantially normal to said exterior surface and connecting said exterior surface and said interior surface, said sensing unit comprising:
   (a) an enclosure including an enclosure exterior, an enclosable interior volume and a portion defining an enclosure aperture connecting said enclosure exterior with said interior volume, said enclosure arranged for securing to said exterior of said duct wall with said enclosure aperture and said duct aperture arranged to provide a passage for communicating fluid in said duct with said interior volume;
   (b) a first sensor located in said interior volume of said enclosure, said first sensor in contact with said fluid and responsive to a first parameter of said fluid in said interior volume of said enclosure;
   (c) a sensor beam rotatably cantilevered and projecting from said enclosure and insertable into said interior of said duct through said duct aperture and said enclosure aperture when said enclosure is secured to said exterior of said duct wall;
   (d) a second sensor responsive to a second parameter of said fluid in said duct and supported in said interior of said duct and distal of said enclosure by said sensor beam; and
   (e) a third sensor responsive to a third parameter of said fluid in said duct and supported in said interior of said duct and distal of said enclosure by said sensor beam.

7. The sensing unit of claim 6 wherein said first sensor is responsive to carbon dioxide in said fluid in said interior volume.

8. The sensing unit of claim 6 wherein said second sensor is responsive to a humidity of said fluid in said duct.

9. The sensing unit of claim 6 wherein said third sensor is responsive to a temperature of said fluid in said duct.

10. The sensing unit of claim 6 wherein said sensor beam further comprises a web arranged to divide said enclosure aperture.

11. The sensing unit of claim 6 wherein said rotatable sensor beam further comprises a stop portion engageable with a portion of said enclosure to limit rotation of said sensor beam to less than one revolution.

12. The sensing unit of claim 6 further comprising a sensor housing hingedly attached to said sensor beam.

13. The sensing unit of claim 12 wherein said sensor housing includes a portion defining a grill aperture enabling communication of fluid in said duct with an interior of said sensor housing.

14. The sensing unit of claim 13 further comprising a screen having a portion defining an opening smaller than said grill aperture, said screen detachably engageable with a surface of said interior of said sensor housing.

* * * * *

UNITED STATES PATENT AND TRADEMARK OFFICE
CERTIFICATE OF CORRECTION

| | | |
|---|---|---|
| PATENT NO. | : 8,024,986 B2 | Page 1 of 1 |
| APPLICATION NO. | : 12/218680 | |
| DATED | : September 27, 2011 | |
| INVENTOR(S) | : Casey Pettit et al. | |

It is certified that error appears in the above-identified patent and that said Letters Patent is hereby corrected as shown below:

On the Title Page, Field (75)

Change "Mathew Vernon" to read --Matthew Vernon--.

Col. 3, Line 1

Change "enclosure can be reduce the" to read --enclosure can reduce the--.

Signed and Sealed this
First Day of May, 2012

David J. Kappos
*Director of the United States Patent and Trademark Office*